United States Patent
Khalaj Amineh et al.

(10) Patent No.: US 9,488,749 B2
(45) Date of Patent: Nov. 8, 2016

(54) HOLOGRAPHIC TECHNIQUES FOR CORROSION EVALUATION OF WELLBORE PIPES

(71) Applicant: Halliburton Energy Services, Inc., Houston, TX (US)

(72) Inventors: Reza Khalaj Amineh, Houston, TX (US); Luis Sanmartin, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/888,483

(22) PCT Filed: Jul. 8, 2015

(86) PCT No.: PCT/US2015/039573
§ 371 (c)(1),
(2) Date: Nov. 2, 2015

(87) PCT Pub. No.: WO2016/007642
PCT Pub. Date: Jan. 4, 2016

(65) Prior Publication Data
US 2016/0161627 A1    Jun. 9, 2016

Related U.S. Application Data

(60) Provisional application No. 62/023,424, filed on Jul. 11, 2014.

(51) Int. Cl.
*G01V 3/28* (2006.01)
*G01V 3/38* (2006.01)
(Continued)

(52) U.S. Cl.
CPC ............... *G01V 3/28* (2013.01); *E21B 12/02* (2013.01); *E21B 47/0006* (2013.01);
(Continued)

(58) Field of Classification Search
None
See application file for complete search history.

(56) References Cited

U.S. PATENT DOCUMENTS 3,437,810 A * 4/1969 Walters ................. E21B 47/082
  250/358.1
3,940,689 A * 2/1976 Johnson, Jr. .......... E21B 47/082
  324/221

(Continued)

FOREIGN PATENT DOCUMENTS

WO    2016007642 A1    1/2016

OTHER PUBLICATIONS

Arbuzov et al., Memory Magnetic Imaging Defectoscopy, SPE 162054, 2012.
(Continued)

*Primary Examiner* — Edward Cosimano
(74) *Attorney, Agent, or Firm* — McDermott Will & Emery LLP; Scott Richardson

(57) ABSTRACT

A method includes obtaining a first small defect response at a given frequency of a first small defect on a first wellbore pipe positioned within a wellbore. A Fourier transform of the first small defect response is then calculated, and a first measured response at the given frequency of a first arbitrary metal loss defect in the first wellbore pipe is obtained with a sensor of a pipe inspection tool. A Fourier transform of the first measured response is then calculated, and a magnitude of the first arbitrary metal loss based on the Fourier transform of the first small defect response and the Fourier transform of the first measured response is then estimated.

18 Claims, 8 Drawing Sheets

(51) Int. Cl.
*G01B 7/06* (2006.01)
*G06F 17/40* (2006.01)
*G06F 19/00* (2011.01)
*E21B 47/08* (2012.01)
*E21B 12/02* (2006.01)
*E21B 47/00* (2012.01)
*G01V 1/28* (2006.01)
*G01N 27/90* (2006.01)

(52) U.S. Cl.
CPC .............. *E21B 47/082* (2013.01); *G01B 7/06* (2013.01); *G01V 3/38* (2013.01); *G01N 27/9046* (2013.01); *G01V 1/28* (2013.01); *G06F 17/40* (2013.01); *G06F 19/00* (2013.01)

(56) References Cited

U.S. PATENT DOCUMENTS

| | | |
|---|---|---|
| 4,292,589 A | 9/1981 | Bonner |
| 5,270,647 A | 12/1993 | Beissner et al. |
| 6,205,859 B1 | 3/2001 | Kwun et al. |
| 7,960,969 B2 * | 6/2011 | Mouget ............... G01V 3/28 324/221 |
| 8,326,549 B2 * | 12/2012 | Ishizaki ............ G05B 23/0283 702/34 |
| 2006/0202685 A1 | 9/2006 | Barolak et al. |
| 2009/0195244 A1 | 8/2009 | Mouget et al. |
| 2010/0179772 A1 * | 7/2010 | Ishizaki ............ G05B 23/0283 702/34 |

OTHER PUBLICATIONS

Garcia, et al., Successful Application of a New Electromagnetic Corrosion Tool for Well Integrity Evaluation in Old Wells Completed with Reduced Diameter Tubular, IPTC 16997, 2013.

Goodman, J.W., Introduction to Fourier Optics (McGraw-Hill, 1996).

International Search Report and Written Opinion for PCT/US2015/039573 dated Sep. 24, 2015.

* cited by examiner

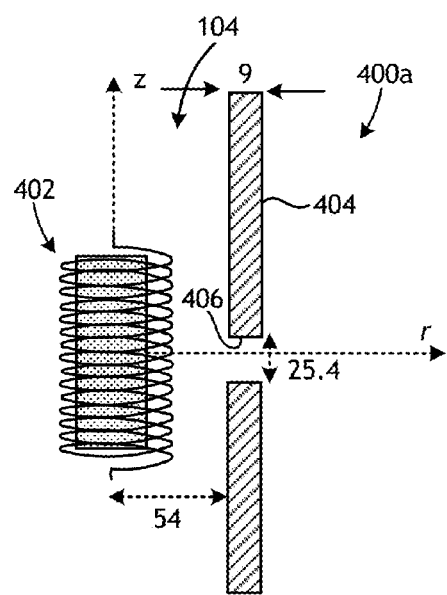
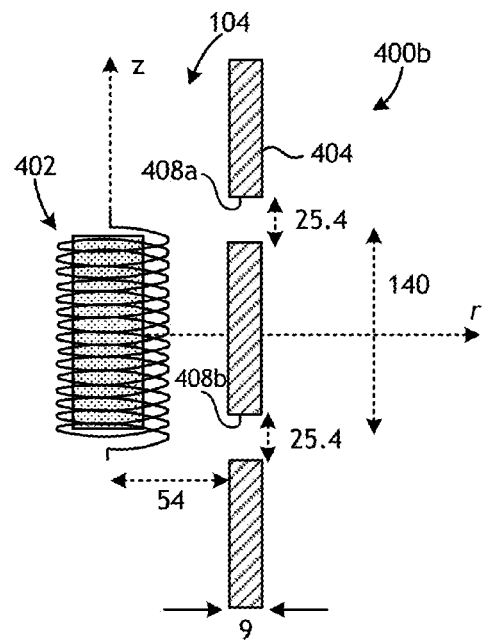
FIG. 4A
FIG. 4B
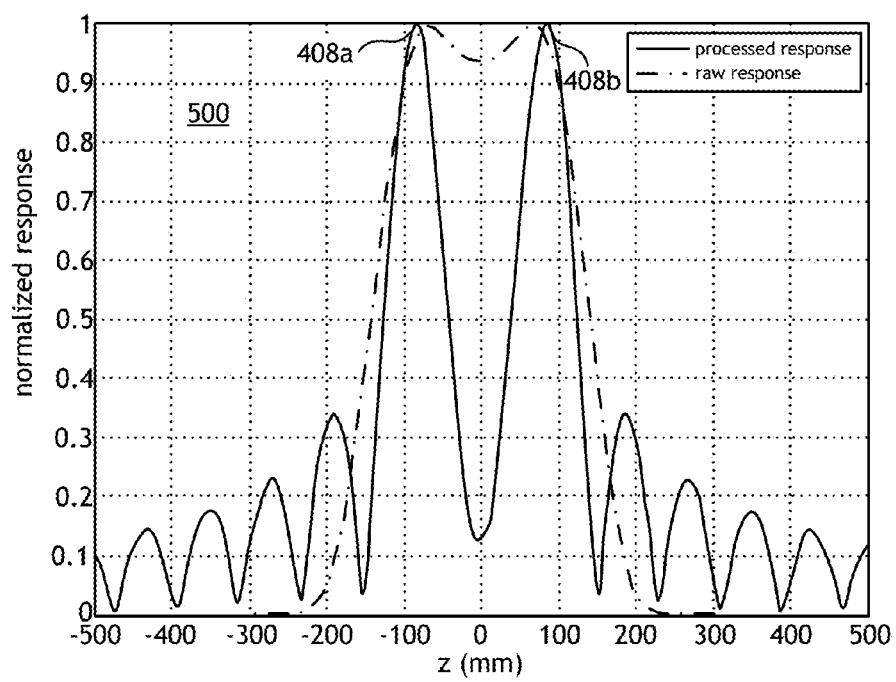
FIG. 5

HOLOGRAPHIC TECHNIQUES FOR CORROSION EVALUATION OF WELLBORE PIPES

CROSS-REFERENCE TO RELATED APPLICATIONS

The present application claims priority to U.S. Provisional Patent App. Ser. No. 62/023,424, filed on Jul. 11, 2014.

BACKGROUND

After drilling a wellbore in the oil and gas industry, the drilled wellbore can be subsequently completed by cementing a string of metal pipes connected end-to-end within the wellbore. Commonly called "casing," such pipes increase the integrity of the wellbore and provide a flow path between the earth's surface and selected subterranean formations. Some wellbores are lined with multiple concentrically-positioned pipes (i.e., concentric strings of casing). Moreover, in some wellbores, one or more production pipes are extended into a cased wellbore to provide a conduit for hydrocarbons to be conveyed to the earth's surface. Accordingly, as used herein, the term "pipe" or "wellbore pipe" will refer to metal pipes or pipelines that line the walls of a wellbore, such as casing, and may also refer to production pipes extended into a wellbore to facilitate hydrocarbon production operations.

During the lifetime of a well, wellbore pipes are exposed to high volumes of materials and fluids required to pass through them, including chemically aggressive fluids. In harsh environments, the pipes may be subject to corrosion that may affect their functionality. Consequently, the structural integrity of wellbore pipes may change over time due to chemical and mechanical interactions. Moreover, due to the length, volume, accessibility difficulties, and long time periods associated with the process, it is a costly task to monitor wellbore pipes and pipelines and intervene when required.

Electromagnetic (EM) sensing technologies and techniques have been developed for such monitoring applications and can generally be categorized into two groups: frequency-domain techniques and time-domain techniques. In frequency-domain techniques, measurements of the wellbore pipes are typically performed at a high frequency to characterize the innermost pipes and at a low frequency to characterize the outermost wellbore pipes. Time-domain techniques are based on the pulse eddy current and employ the transient response (decay response versus time) of the pipes to a pulse excitation. Proper analysis of the signal responses can determine metal losses in the pipes with better resolutions, and also improve the robustness of the characterization process to noise.

While EM sensing provides continuous, in situ measurements of the integrity of wellbore pipes, the available EM inspection tools do not effectively facilitate evaluation of multiple concentrically-positioned wellbore pipes.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 4A and 4B are schematic diagrams of corresponding wellbore zones where a first simulation example is undertaken.

FIG. 5 is a plot showing holographic imaging of the pipe of FIG. 4B as compared to raw responses.

DETAILED DESCRIPTION

The present disclosure is related to maintenance of wellbores in the oil and gas industry and, more particularly, to monitoring and evaluating corrosion in wellbore pipes, such as strings of casing or production tubing.

The embodiments disclosed herein describe holographic one-dimensional imaging techniques that improve the resolution of defect evaluation when using longer coil antennas for inspecting multiple concentrically-positioned wellbore pipes, such as casing or production tubing. The presently disclosed measurement tools and methods provide better resolution for monitoring the condition of wellbore pipes since small dimensional features of flaws, defects, and metal losses can be resolved with better accuracy. Moreover, while maintaining a good resolution, larger illuminating sources or sensors can be employed in accordance with the present embodiments, thereby allowing for monitoring multiple wellbore pipes with larger outer diameters.

The presently described methods acquire responses at multiple frequencies when employing frequency-domain eddy current technique. Alternatively, they acquire time-domain responses when employing pulse eddy current technique and convert time-domain data to frequency-domain data. Subsequently, presently described methods apply a multiple frequency holographic inversion algorithm. As a result, the robustness-to-noise may be improved significantly. Lastly, characterization of the wellbore pipes with better one-dimensional image resolution may provide an operator with a more precise evaluation of these components, and may ultimately lead to a significant positive impact on hydrocarbon production process.

Figure 1:
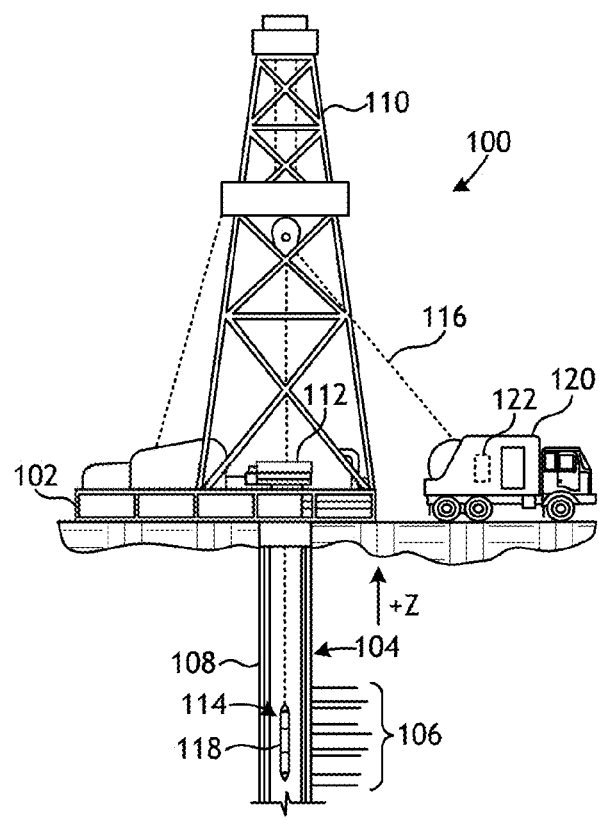
FIG. 1 is a schematic diagram of an exemplary wireline system that may employ the principles of the present disclosure.

FIG. 1 is a schematic diagram of an exemplary wireline system 100 that may employ the principles of the present disclosure, according to one or more embodiments. As illustrated, the wireline system 100 may include a surface platform 102 positioned at the earth's surface and a wellbore 104 that extends from the surface platform 102 into one or more subterranean formations 106. In other embodiments, such as in offshore operations, a volume of water may separate the surface platform 102 and the wellbore 104. The wellbore 104 may be lined with one or more pipes 108, also referred to as strings of casing. In some embodiments, portions of the wellbore 104 may have only one pipe 108 positioned therein, but other portions of the wellbore 104 may be lined with two or more concentrically-disposed pipes 108. The pipes 108 may be made of plain carbon steel, stainless steel, or another material capable of withstanding a variety of forces, such as collapse, burst, and tensile failure.

The wireline system 100 may include a derrick 110 supported by the surface platform 102 and a wellhead installation 112 positioned at the top of the wellbore 104. A pipe inspection tool 114 may be suspended into the wellbore 104 on a cable 116. In some embodiments, the pipe inspection tool 114 may alternatively be suspended within a production pipe (not shown) positioned within the pipes 108 that line the wellbore 104 (i.e., casing). In such embodiments, the production pipe may extend by itself into the pipes 108 or alternatively be positioned adjacent to one or more eccentrically-located production pipes (not shown) that are also positioned within the pipes 108. Accordingly, the pipes 108 may refer to strings of casing that line the wellbore 104 or at least one production pipe.

The pipe inspection tool 114 may comprise an electromagnetic, non-destructive inspection tool. Its operation may be based on either the flux-leakage principle or the eddy-current principle, or a combination thereof, and may be insensitive to non-conductive deposits and is operable irrespective of the nature of the fluid mixture flowing into/out of the wellbore 104. The pipe inspection tool 114 can be used for the detection of localized damage or defects in the pipes 108. In operation, the pipes 108 are subjected to a strong static magnetic field and, due to their ferromagnetic nature, the magnetic return flux is mainly confined to the inside of the pipes 108. In the presence of discontinuities or defects in the metal, such as pits and holes caused by corrosion, the changes in the magnetic field can be detected with the pipe inspection tool 114.

To accomplish this, the pipe inspection tool 114 may include one or more electromagnetic sensors 118, which may be communicably coupled to the cable 116. The cable 116 may include conductors for conveying power to the pipe inspection tool 114 and also for facilitating communication between the surface platform 102 and the pipe inspection tool 114. A logging facility 120, shown in FIG. 1 as a truck, may collect measurements from the electromagnetic sensors 118, and may include computing facilities 122 for controlling, processing, storing, and/or visualizing the measurements gathered by the electromagnetic sensors 118. The computing facilities 122 may be communicably coupled to the pipe inspection tool 114 by way of the cable 116.

The electromagnetic sensors 118 may include one or more electromagnetic coil antennas that may be used as transmitters, receivers, or a combination of both (i.e., transceivers) for obtaining in situ measurements of the pipe(s) 108 and thereby determine the structural integrity or condition of each pipe 108. In some embodiments, the electromagnetic sensors 118 may be designed to operate in a centralized position within the innermost pipe 108, such as through the use of one or more centralizers (not shown) attached to the body of the pipe inspection tool 114. In other embodiments, however, the electromagnetic sensors 118 may be designed to be adjacent to or in intimate contact with the inner wall of the innermost pipe 108. In such embodiments, the electromagnetic sensors 118 may be mounted on one or more deployable sensor pads (not shown) positioned on actuatable arms (not shown) that move the electromagnetic sensors 118 radially outward toward the inner wall of the innermost pipe 108.

Figure 2A:
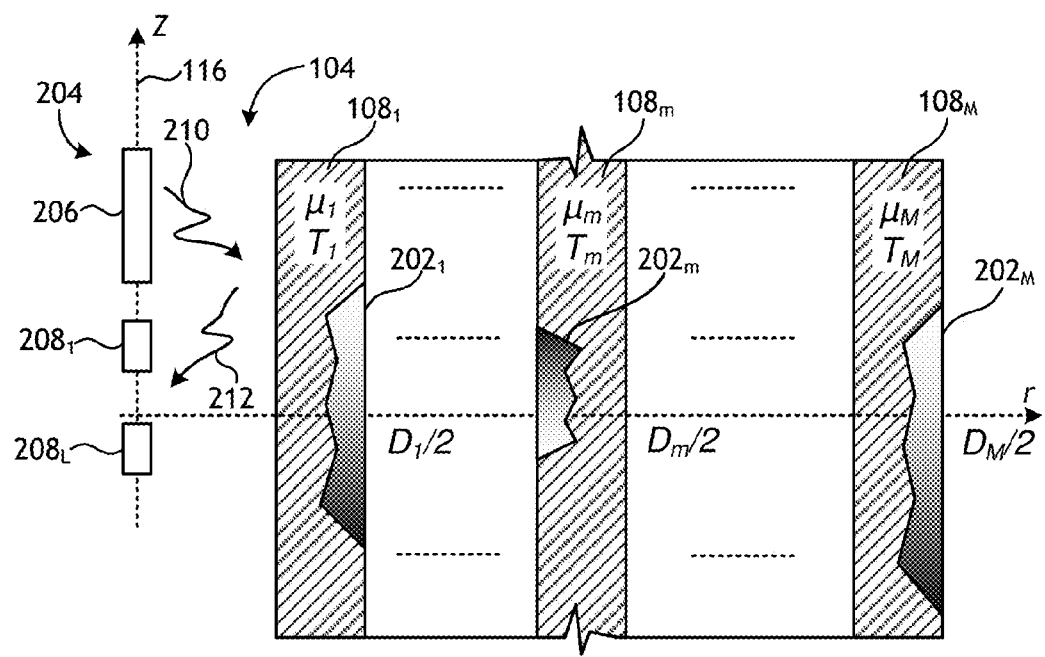
FIG. 2A is a schematic cross-sectional side view of a portion of the wellbore of FIG. 1.

FIG. 2A is a schematic cross-sectional side view of a portion of the wellbore 104, according to one or more embodiments. For simplicity, only one cross-sectional side of the wellbore 104 is shown in FIG. 2A. As illustrated, the wellbore 104 may include multiple pipes positioned therein and referenced as a first pipe $108_1$, a second or m-th pipe $108_m$, and a third or M-th pipe $108_M$ (collectively referred to herein as "pipes 108"). As will be appreciated, usage of m and M is intended to show that any number of pipes 108 may be used, without departing from the scope of the disclosure. In some embodiments, the pipes $108_1$, $108_m$, $108_M$ may each line the wellbore 104 as concentrically-positioned strings of casing. In other embodiments, however, at least the first pipe $108_1$ may comprise a production pipe or tubing positioned within the m-th pipe $108_m$ either concentric or eccentric to the remaining pipes $108_m$, $108_M$.

In the illustrated embodiment, each pipe $108_1$, $108_m$, $108_M$ may include at least one defect, such as a spot or location of corrosion, shown in FIG. 2A as a first defect $202_1$, a second or m-th defect $202_m$, and a third or M-th defect $202_M$. As will be appreciated, the defects $202_1$, $202_m$, $202_M$ may be present on the inner or outer surfaces of the pipes $108_1$, $108_m$, $108_M$, or both.

A pipe inspection tool 204 may be extended into the wellbore 104 and used to monitor the integrity of the pipes $108_1$, $108_m$, $108_M$. The pipe inspection tool 204 may be similar to or the same as the pipe inspection tool 114 of FIG. 1. As illustrated, the pipe inspection tool 204 may include an excitation source 206, such as a transmitter coil or antenna. The pipe inspection tool 204 may also include one or more sensors $208_1$ and $208_L$ such as a receiver coil (alternatively referred to as a receiver antenna). The sensors $208_1$ and $208_L$ are shown in FIG. 2A as a first sensor $208_1$ and an L-th sensor 208, indicating that the pipe inspection tool 204 may include any number ("L") of sensors $208_1$ and $208_L$ without departing from the scope of the disclosure. The excitation source 206 may be configured to produce a magnetic field 210 (i.e., an excitation signal), and the sensors $208_1$-$208_L$ may be configured to detect a return magnetic field 212 (i.e., a response signal) after having interacted with the pipes $108_1$, $108_m$, $108_M$.

The first pipe $108_1$ may have an outer diameter $D_1$, the m-th pipe $108_m$ may have an outer diameter $D_m$, and the M-th pipe $108_M$ may have an outer diameter $D_M$. Moreover, $\mu_1$, $\mu_m$, and $\mu_M$ refer to the relative magnetic permeability of the of the pipes $108_1$, $108_m$, $108_M$, respectively, while $T_1$, $T_m$, and $T_M$ refer to the thickness of the pipes $108_1$, $108_m$, $108_M$, respectively.

According to the present disclosure, measurement data from the pipes $108_1$, $108_m$, $108_M$ may be obtained by the sensors $208_1$-$208_L$ at multiple frequencies along the axial direction z within the wellbore 104 and may be utilized to reconstruct one-dimensional holographic images of the pipes $108_1$, $108_m$, $108_M$. Obtained measurement data may be transmitted to the logging facility 120 (FIG. 1) via the cable 116 for processing and qualitative imaging of the pipes $108_1$, $108_m$, $108_M$. The calculations and algorithms described herein may prove advantageous in enhancing the imaging resolution of any defects on the individual pipes $108_1$, $108_m$, $108_M$, which may help facilitate proper remedial actions for the pipes $108_1$, $108_m$, $108_M$, if needed.

In applying a holographic algorithm used to generate one-dimensional holographic images of the pipes $108_1$, $108_m$, $108_M$, it is assumed that the measurement system of the pipe inspection tool 204 is linear, an assumption that is based on the well-known Born approximation. According to the Born approximation, an incident field is taken in place of a total field as the driving field at each point in a scattering plot, and a linear superposition method is applied to scattering by an extended body. Born approximation can be accurate if the scattered field is small in the scatterer, as compared to the incident field. Normally one would solve Maxwell's equations in three-dimensions to obtain accurate measurement data, but the Born approximation can be sufficiently accurate by approximating Maxwell's equations for scatters that are small (i.e., low scattering).

Figure 2B:
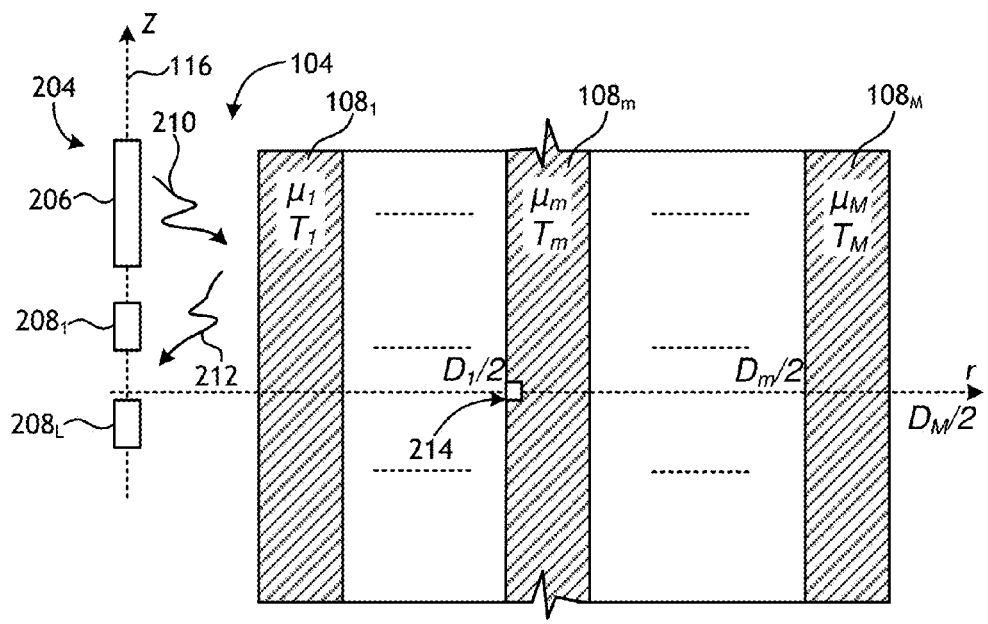
FIG. 2B is a schematic cross-sectional side view of another portion of the wellbore of FIG. 1.

FIG. 2B is another schematic cross-sectional side view of the wellbore 104, according to one or more embodiments. For a linear measurement system, for example, a measured response for a small (but measurable) defect 214 in the m-th pipe $108_m$ may first be obtained. The small defect 214, also referred to herein as a "delta-like defect," may comprise the smallest measureable metal loss region in the m-th pipe $108_m$. The small defect 214 may exhibit various shapes, but should be as small as possible in the order of the resolution of the pipe inspection tool 204 or smaller (in particular along the z direction). Accordingly, the small defect 214 may be small, but sufficiently large to be measured by the pipe inspection tool 204.

Once a measured response to the small defect 214 is obtained, measured responses for any other investigated defect or metal loss region (i.e., the defects $202_1$, $202_m$, $202_M$ of FIG. 2A) can be computed. In some embodiments, a response for the small defect 214 may be obtained by running a surface experiment under laboratory conditions to simulate the small defect 214. In other embodiments, however, the small defect 214 can be physically measured using the pipe inspection tool 204 or another sensor device. The small defect 214 can be approximated with a Dirac delta function at a radial distance of $D_m/2$, i.e., $\delta(z, D_m/2)$, where z is the axial position along the m-th pipe and $D_m/2$ is the radial (r) position away from the pipe inspection tool 204 assuming that the small defect 214 is at z=0. In mathematics, the Dirac delta function is a distribution on the real number line that is zero everywhere except at zero, with an integral of one over the entire real line.

The response measured by a generic sensor over the z-axis at a single frequency ω is denoted by $h(z, D_m/2, \omega)$. The measured response $h(z, D_m/2, \omega)$ may be calibrated such that it includes the response due to the small defect 214 only and not due to the pipes $108_1$, $108_m$, $108_m$. This may be accomplished by recording the response over the z-axis twice; once with the presence of the small defect 214 and once without the presence of the small defect 214, and then the difference of these two responses may be calculated to obtain a calibrated response "r". Accordingly, the calibrated response r due to any arbitrary metal loss or defect function $x(z, D_m/2)$ in the m-th pipe $108_m$, such as the m-th defect $202_m$ (FIG. 2A), may be written in terms of the delta-like defect response $h(z, D_m/2, \omega)$ as follows:

$$r(z,\omega) \approx x(z, D_m/2) * h(z, D_m/2, \omega) \quad \text{Equation (1)}.$$

The "*" in Equation (1) denotes a convolution operation along the z direction and ω denotes the operation frequency. The defect function $x(z, D_m/2)$ includes the effect of equivalent metal loss at that particular z position. By taking the Fourier transform of both sides of Equation (1) with respect to the z variable, Equation (2) is derived as follows:

$$R(k_z,\omega) \approx X(k_z, D_m/2) H(k_z, D_m/2, \omega) \quad \text{Equation (2)}.$$

The R, X, and H of Equation (2) are Fourier transforms of the calibrated response function r, the defect function x, and the measured response function h, respectively, and $k_z$ is the Fourier variable corresponding to the z direction. From Equation (2), it is observed that if the measured response h is obtained due to a delta-like defect in the m-th pipe $108_m$ beforehand, and if the response due to an arbitrary metal loss function x in the same m-th pipe $108_m$ is measured, one can then estimate this metal loss function. This can be performed for any arbitrary metal loss, such as the m-th defect $202_m$ (FIG. 2A).

If calibrated responses R have been collected at N frequencies (for both delta-like and tested defects), writing Equation (2) leads to the following system of equations:

$$\begin{bmatrix} R(k_z, \omega_1) \\ \vdots \\ R(k_z, \omega_N) \end{bmatrix} \approx \begin{bmatrix} H(k_z, D_m/2, \omega_1) \\ \vdots \\ H(k_z, D_m/2, \omega_N) \end{bmatrix} X(k_z, D_m/2). \quad \text{Equation (3)}$$

The system of equations provided in Equation (3) can be solved for $X(k_z, D_m/2)$ in the least squares sense. Such separate systems of equations have to be solved for all $k_z$ values, and once they are solved, the reconstruction image of the tested defect $x(z, D_m/2)$ may be obtained by taking the inverse Fourier transform of $X(k_z, D_m/2)$ with respect to the $k_z$ variable.

If time-domain data acquisition has been adapted (like in pulse eddy current) for a particular application, the Fourier transform of the collected data can be implemented to obtain frequency-domain data. Then, by proper sampling of the data in the frequency domain, one can construct the system of equations provided in Equation (3). As will be appreciated, using multiple frequency data may prove advantageous in improving the robustness-to-noise for the pipe inspection tool 204.

The foregoing discussion is related to evaluating defects (i.e., corrosion) on a single pipe, such as the m-th pipe $108_m$. It will be appreciated, however, that the imaging techniques of the present disclosure may be extended to applications where it may be necessary to inspect defects on multiple pipes, such as any of the pipes $108_1$, $108_m$, $108_M$. In such applications, the calibrated response R described above may be approximated using the superposition principle. Briefly, the superposition principle states that, for all linear systems, the net response at a given place and time caused by two or more stimuli is the sum of the responses that would have been caused by each stimulus individually. A linear function is one that satisfies the properties of superposition.

In other words, the calibrated response R may be obtained from the sum of the individual responses due to the corrosion on each pipe $108_1$, $108_m$, $108_M$. Thus, assuming imaging of the metal loss variation for each pipe $108_1$, $108_m$, $108_M$ is desired, Equation (2) may be rewritten as:

$$R(k_z,\omega) \approx X(k_z,D_1/2)H(k_z,D_1/2,\omega) + \ldots + X(k_z,D_M/2)H(k_z,D_M/2,\omega) \quad \text{Equation (4)}.$$

Writing Equation (4) at N frequencies leads to:

$$\begin{bmatrix} R(k_z, \omega_1) \\ \vdots \\ R(k_z, \omega_N) \end{bmatrix} \approx \begin{bmatrix} H(k_z, D_1/2, \omega_1) & \cdots & H(k_z, D_M/2, \omega_1) \\ \vdots & \ddots & \vdots \\ H(k_z, D_1/2, \omega_N) & & H(k_z, D_M/2, \omega_N) \end{bmatrix} \quad \text{Equation (5)}$$

$$\begin{bmatrix} X(k_z, D_1/2) \\ \vdots \\ X(k_z, D_M/2) \end{bmatrix}.$$

This system of equations can be solved for $X(k_z, D_m/2)$, $m=1, 2, \ldots, M$ in the least squares sense. Such separate systems of equations have to be solved for all $k_z$ values, and once they are solved, the reconstruction of the image of the pipes $x(z, D_m/2)$, $m=1, 2, \ldots, M$ may be obtained by taking the inverse Fourier transform of $X(k_z, D_m/2)$, $m=1, \ldots, M$ with respect to the $k_z$ variable.

Furthermore, it may be possible to acquire data with multiple sensors, such as any of the sensors $208_1$-$208_L$. When employing multiple sensors $208_1$-$208_L$, Equation (4) above may be written for each sensor $208_1$-$208_L$ as follows:

$$\begin{cases} R_1(k_z, \omega) \approx X(k_z, D_1/2)H_1(k_z, D_1/2, \omega) + \ldots + \\ \qquad X(k_z, D_M/2)H_1(k_z, D_M/2, \omega) \\ \vdots \\ R_L(k_z, \omega) \approx X(k_z, D_1/2)H_L(k_z, D_1/2, \omega) + \ldots + \\ \qquad X(k_z, D_M/2)H_L(k_z, D_M/2, \omega) \end{cases} \quad \text{Equation (6)}$$

In Equation (6), $H_L(k_z, D_m/2, \omega)$ is the Fourier transform of the calibrated delta-like defect response measured by the L-th sensor $208_L$ and for the small (delta-like) metal loss on the m-th pipe $108_m$. Since the unknowns $X(k_z, D_m/2)$, $m=1, \ldots, M$ are common for all the equations above, a single system of equations can be derived as:

$$\begin{bmatrix} R_1(k_z, \omega_1) \\ \vdots \\ R_1(k_z, \omega_N) \\ \vdots \\ R_L(k_z, \omega_1) \\ \vdots \\ R_L(k_z, \omega_N) \end{bmatrix} \approx \quad \text{Equation (7)}$$

$$\begin{bmatrix} H_1(k_z, D_1/2, \omega_1) & \ldots & H_1(k_z, D_M/2, \omega_1) \\ \vdots & \ddots & \vdots \\ H_1(k_z, D_1/2, \omega_N) & \ldots & H_1(k_z, D_M/2, \omega_N) \\ \vdots & & \vdots \\ H_L(k_z, D_1/2, \omega_1) & \ldots & H_L(k_z, D_M/2, \omega_1) \\ \vdots & \ddots & \vdots \\ H_L(k_z, D_1/2, \omega_N) & \ldots & H_L(k_z, D_M/2, \omega_N) \end{bmatrix}$$

$$\begin{bmatrix} X(k_z, D_1/2) \\ \vdots \\ X(k_z, D_M/2) \end{bmatrix}.$$

The system of equations in Equation (7) can be solved for $X(k_z, D_m/2)$, $m=1, \ldots, M$ in the least squares sense. Such separate systems of equations have to be solved for all $k_z$ values, and once they are solved, the reconstruction of the images of the pipes $x(z, D_m/2)$, $m=1, \ldots, M$ may be obtained by taking the inverse Fourier transform of $X(k_z, D_m/2)$, $m=1, \ldots, M$ with respect to the $k_z$ variable.

As will be appreciated, the dimensions and/or configuration of the sensors $208_1$-$208_L$ may be altered to measure from the innermost pipe up to any particular number of pipes $108_1$, $108_m$, $108_M$. More particularly, some of the sensors $208_1$-$208_L$ may be smaller or shorter than other sensors $208_1$-$208_L$ and, therefore, may be configured to measure the responses derived from a particular number of innermost pipes, for example only the first pipe $108_1$. As a result, this may simplify the imaging process for the first pipe $108_1$ and provide a more precise estimate for the first pipe $108_1$ and others that are radially adjacent. These estimations can then be used to image the outer pipes, such as the m-th pipe $108_m$ to the M-th pipe $108_M$, with better accuracy when acquiring the data from those pipes with proper choice of sensors and frequencies.

In the disclosed holographic imaging approaches describe above, it is assumed that the calibrated delta-like response is known a priori. This data can be recorded beforehand by measuring delta-like (small) metal loss regions or small holes for various numbers of pipes $108_1$, $108_m$, $108_M$ with variable magnetic permeability, thickness, and outer diameters. Such data can be stored in a library or database that may be accessed with the processing modules used to undertake the presently described methods. Alternatively, this information can be obtained from a proper forward model through simulations.

In order to image any of the defects $202_1$, $202_m$, $202_M$ of FIG. 2A (i.e., metal loss regions), a pre-requisite step is to estimate the relative magnetic permeability $\mu_1$, $\mu_m$, $\mu_M$ of the pipes $108_1$, $108_m$, $108_M$. This allows for using the previously recorded delta-like responses stored in the library (database) corresponding to the relative magnetic permeability $\mu_1$, $\mu_m$, $\mu_M$ values. When acquiring data at multiple frequencies, the data at higher and lower frequencies can be employed to estimate the magnetic permeability $\mu$ values for innermost and outermost pipes $108_1$, $108_m$, $108_M$, respectively. When acquiring data in the time-domain, the decay responses can be processed. Magnetic permeability $\mu$ values for the outer pipes, such as the pipes $108_m$ and $108_M$, affect the response at longer decay times.

Figure 3:
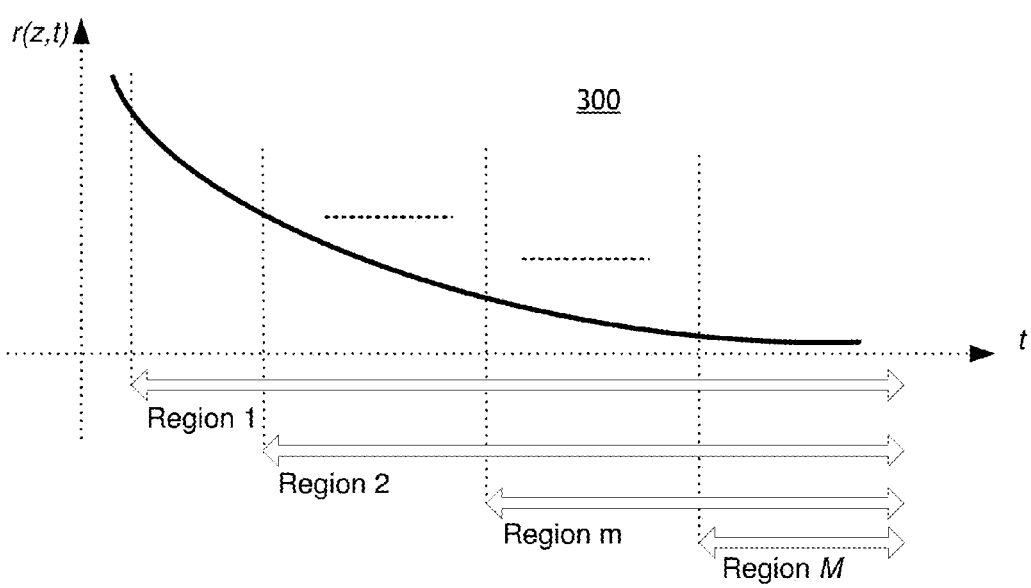
FIG. 3 is a plot showing the decay response of a pulse eddy current technique that can be used in estimation of magnetic permeability of innermost and outermost pipes.

It is possible to first estimate the magnetic permeability $\mu$ of the inner most pipes from smaller or shorter sensors $208_1$-$208_L$ and then, by having these values, estimate the magnetic permeability $\mu$ of the outermost pipes from the data acquired by larger or longer sensors $208_1$-$208_L$. It is also possible to estimate the magnetic permeability $\mu$ of all the pipes from the data acquired from the larger or longer sensors $208_1$-$208_L$. In the frequency-domain eddy current, this can be performed by processing the high frequency data to estimate the magnetic permeability of the innermost pipes and use them and the data acquired at lower frequencies to estimate the magnetic permeability of the outermost pipes. Alternatively, magnetic permeability of all pipes can be estimated from the data acquired at low frequencies. In the time-domain eddy current, this can be performed by dividing the decay response of the sensor into M regions, as shown in the plot 300 of FIG. 3, such that at the beginning of the m-th sub-region the response due to the m-th pipe $108_m$ may be observed. Then, by properly processing the values of the decay response at these sub-regions, the magnetic permeability of the pipes $108_1$, $108_m$, $108_M$ can be estimated.

In a traditional well logging process, it may not be practical to apply the foregoing methods for the entire well log in one shot because of the numerical cost and the stability issues. However, at selected depths within the wellbore 104, a monitoring window may be defined and centered at the selected depths and the above-described holographic inversion algorithm may be solved at each depth. A separate depth range may be defined for the solution to the holographic algorithm. After the results at each depth are computed (e.g., at the logging facility 120 or FIG. 1 or elsewhere), the results may be combined to obtain a single and complete one-dimensional log along the selected depths.

Since the presently-described approach is based on the Born approximation, it is valid when the defects in the pipes $108_1$, $108_m$, $108_M$ are small. Due to the same reasoning, the results derived from the present embodiments are qualitative and can be employed only for imaging purposes without precisely estimating the thickness $T_1$, $T_m$, and $T_M$ of the pipes $108_1$, $108_m$, $108_M$. The metal loss function x provides an approximate evaluation of the extent of the defects $202_1$, $202_m$, $202_M$ (FIG. 2A).

In addition, the accuracy and resolution of the presently disclosed techniques may depend on the measurement of the delta-like defect response h. The defect for which the delta-like defect response h is measured, represents the smallest defect that can be imaged by the system. In other words, it determines the size of each pixel in the resulting image. Any larger defects can then be imaged with similar pixel size. In the present embodiments, the variation of the delta-like defect response h with the radial distance over the thickness $T_1$, $T_m$, and $T_M$ of the pipes $108_1$, $108_m$, $108_M$ is not discussed. Alternatively, the delta-like defect response h can be measured over the radial distance within the pipes $108_1$, $108_m$, $108_M$ and this variation can be included in the image reconstruction process.

To show the performance of the presently disclosed methods, the following two simulation examples are provided. The following simulations are provided for illustrative purposes in describing the present subject matter and should in no way be considered limiting to the present disclosure.

Table 1 below provides the dimensions of transmitter and receiver coil antennas used in the first and second simulation examples, and Table 2 provides the dimensions of the core of each transmitter and receiver coil antenna.

TABLE 1

|  | Radius (in.) | Length (in.) | # of Turns |
| --- | --- | --- | --- |
| Transmitter | 0.568 | 9.5 | 1 |
| Receiver | 0.5 | 9.5 | 1 |

TABLE 2

|  | Radius (in.) | Length (in.) | Conductivity | Relative Permeability |
| --- | --- | --- | --- | --- |
| Core | 0.355 | 9 | $1 \times 10^5$ | 1500 |

FIGS. 4A and 4B are schematic diagrams of wellbore zones 400a and 400b, respectively, where the first simulation example is undertaken. In FIGS. 4A and 4B, a pipe inspection tool 402 is lowered into the wellbore 104 that includes a single pipe 404. In FIG. 4A, the pipe 404 includes a first metal loss region 406, which comprises a 25.4 mm (1 inch) hole through the pipe 404. In FIG. 4B, the pipe 404 includes a second metal loss region 408a and a third metal loss region 408b, where each metal loss region 408a,408b comprises a 25.4 mm (1 inch) hole through the pipe 404 at corresponding locations.

In the first simulation example, the acquired responses are processed to improve the imaging resolution for the pipe 404, which exhibits a conductivity of $\sigma=3.4\times10^6$ and a relative magnetic permeability of $\mu_r=116$. To obtain the delta-like defect response, the received responses were simulated over the z-axis for the first metal loss region 406, as shown in FIG. 4A. The simulations were performed at a frequency of 200 Hz. As a tested case, the configuration shown in FIG. 4B was considered where the first and second metal loss regions 408a,408b are to be imaged. The responses for the first and second metal loss regions 408a, 408b were acquired at the same frequency (i.e., 200 Hz) over the z-axis.

FIG. 5 is a plot 500 showing holographic imaging of the pipe 404 of FIG. 4B as compared to raw responses. After applying the holographic image reconstruction algorithm discussed herein, the two metal loss regions 408a,408b are depicted in contrast with the raw response. More particularly, as compared to the raw response, the peaks of the metal loss regions 408a,408b are prominently displayed at about −90 mm and about +90 mm, respectively. Accordingly, by applying the processing techniques described herein, improved resolution for one-dimensional pipe defect images may be obtained.

Figure 6A:
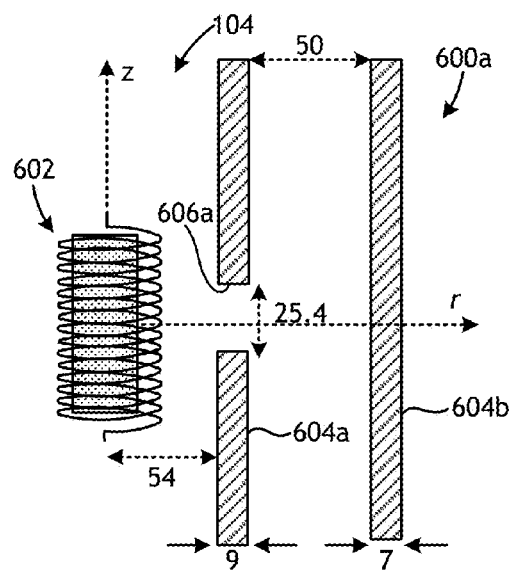
FIGS. 6A-6C are schematic diagrams of corresponding wellbore zones where a second simulation example is undertaken.
Figure 6B:
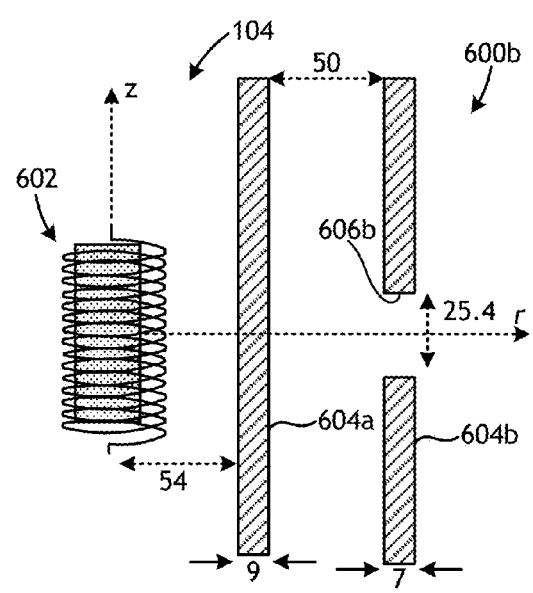
Figure 6C:
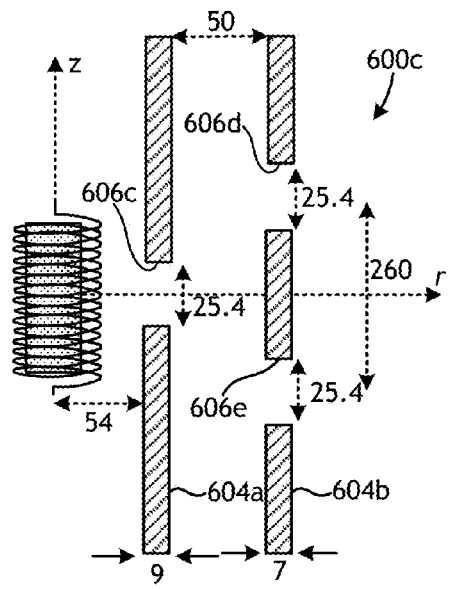

FIGS. 6A-6C are schematic diagrams of wellbore zones 600a, 600b, and 600c, respectively, where the second simulation example is undertaken. In FIGS. 6A and 6B, a pipe inspection tool 602 is lowered into the wellbore 104 that includes a first pipe 604a and a second pipe 604b. In FIG. 6A, the first pipe 604a includes a first metal loss region 606a, and in FIG. 6B, the second pipe 604b includes a second metal loss region 606b, where each metal loss region 606a,606b comprises a 25.4 mm (1 inch) hole through the first and second pipes 604a,604b, respectively. In FIG. 6C, the first pipe 604a includes a third metal loss region 606c and the second pipe 604b includes fourth and fifth metal loss regions 606d and 606e, respectively, where each metal loss region 606c,606d,606e comprises a 25.4 mm (1 inch) hole through the corresponding pipes 604a,604b at corresponding locations.

In the second simulation example, the acquired responses were processed to improve the resolution of the imaging for applications that include double pipes 604a,604b, each of which exhibit a conductivity of $\sigma=3.4\times10^6$ and a relative magnetic permeability of $\mu_r=20$. To obtain the delta-like defect responses, the received responses were simulated over the z-axis once for the first metal loss region 606a on the first pipe 604a and then once for the second metal loss region 606b on the second pipe 604b, and thereby obtaining two delta-like defect responses required for the holographic imaging. The simulations for the second example were performed at eight frequencies of 2 Hz, 5 Hz, 15 Hz, 30 Hz, 50 Hz, 80 Hz, 100 Hz, and 200 Hz.

Figure 7:
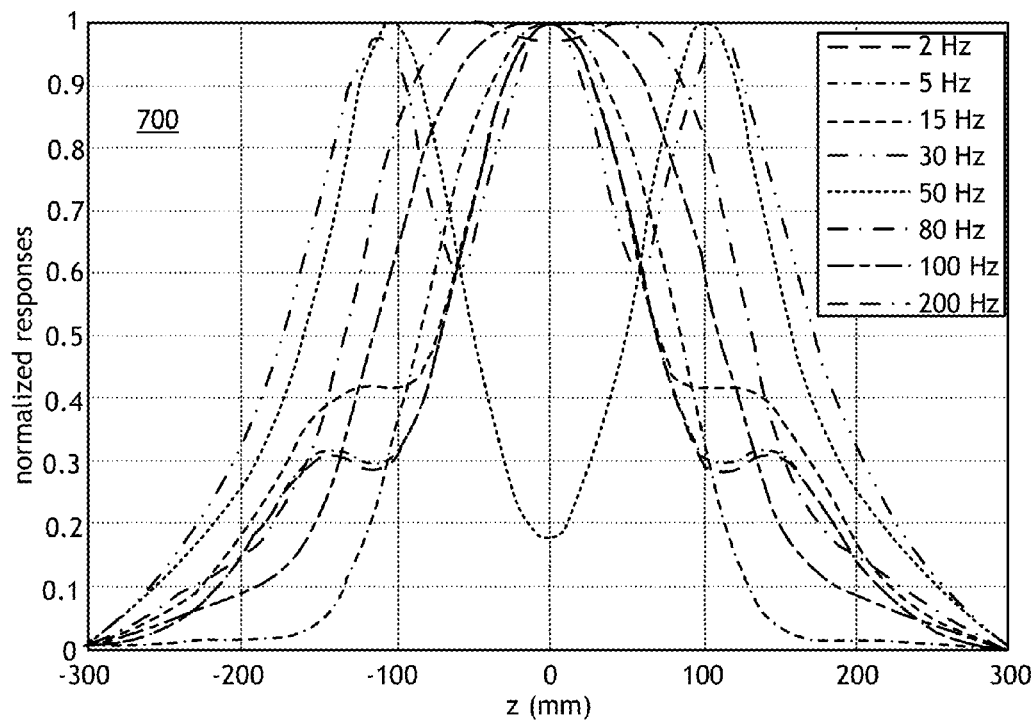
FIG. 7 is a plot that shows normalized raw responses obtained at various frequencies for the wellbore zone of FIG. 6C.

As the tested case, the wellbore zone 600c of FIG. 6C was considered, where the third, fourth, and fifth metal loss regions 606c,606d,606e are to be imaged. The responses for the third, fourth, and fifth metal loss regions 606c,606d,606e were acquired at the same frequencies as those for the delta-like responses over the z-axis. FIG. 7 is a plot 700 that shows the normalized raw responses obtained at the various frequencies for the wellbore zone 600c of FIG. 6C.

Figure 8A:
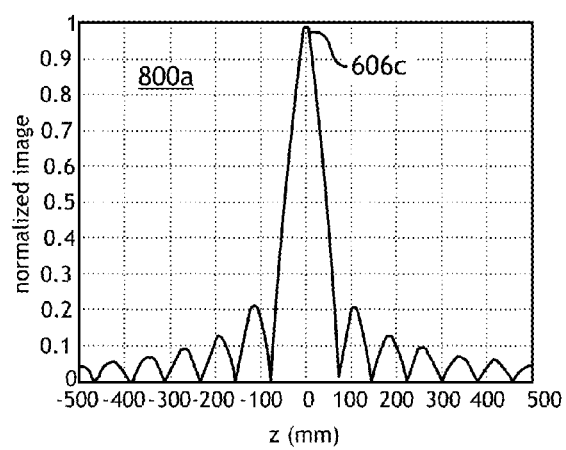
FIGS. 8A and 8B are plots that show reconstructed images of the third, fourth, and fifth metal loss regions of the wellbore zone of FIG. 6C.
Figure 8B:
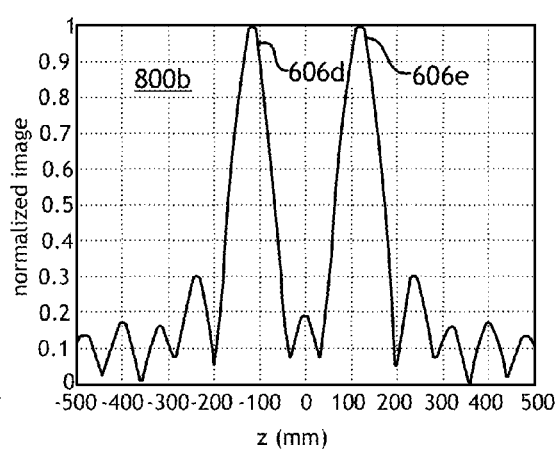

FIGS. 8A and 8B are plots 800a and 800b that show reconstructed images of the third, fourth, and fifth metal loss regions 606c,606d,606e of the wellbore zone 600c of FIG. 6C after applying the presently disclosed holographic image reconstruction algorithm. More particularly, FIG. 8A depicts a reconstructed one-dimensional image of the third metal loss region 606c on the first pipe 604a, and FIG. 8B depicts a reconstructed one-dimensional image of the fourth and fifth metal loss regions 606d,606e on the second pipe 604b. As will be appreciated, the accuracy of the imaging process can be improved further by acquiring the responses at a wider range and larger number of frequencies and over larger scanned depths.

In order to demonstrate the efficiency of the presently described methods in improving image resolution, the processed images may be compared with raw responses. It is well-known that the response at higher frequencies can be employed to investigate the innermost pipes (i.e. the first pipe 604a) and the responses at lower frequencies can be employed to investigate conditions of external or outermost pipes (i.e., the second pipe 604b).

Figure 9:
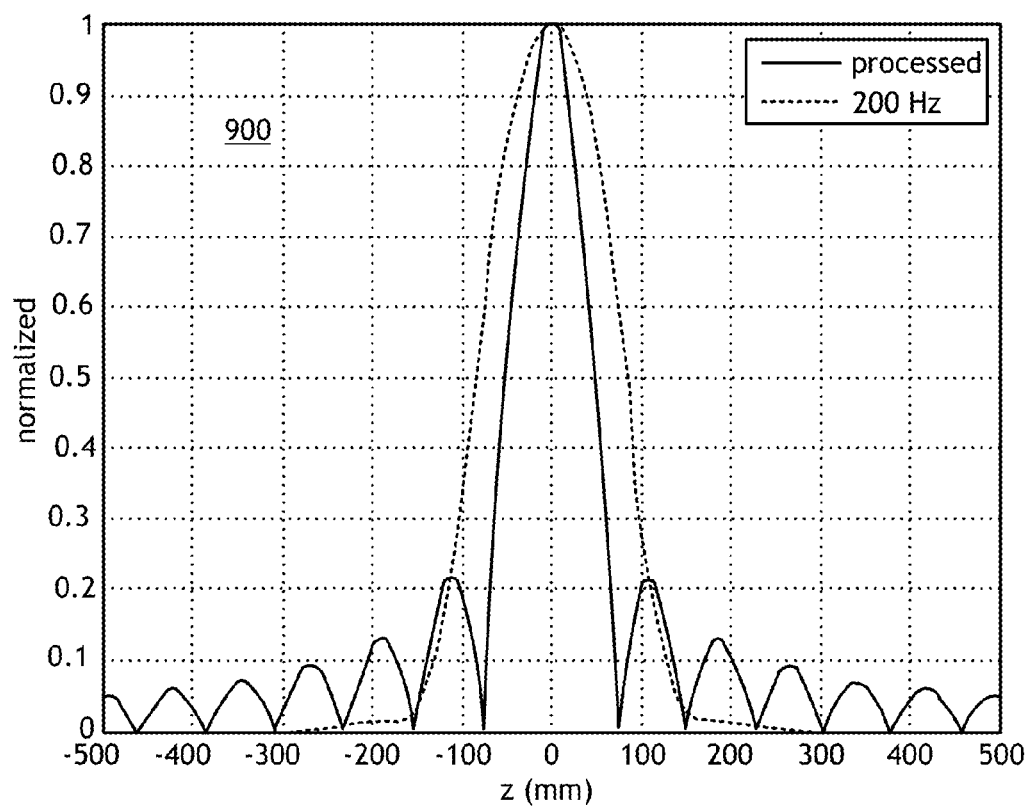
FIG. 9 is a plot that compares the processed image of the first pipe of FIG. 6C with the raw response at 200 Hz.

FIG. 9 is a plot 900 that compares the processed image of the first pipe 604a with the raw response at 200 Hz. In FIG. 9, it is observed that although the raw response at 200 Hz still shows the existence of one defect, the resolution has been improved significantly for the processed image.

Figure 10:
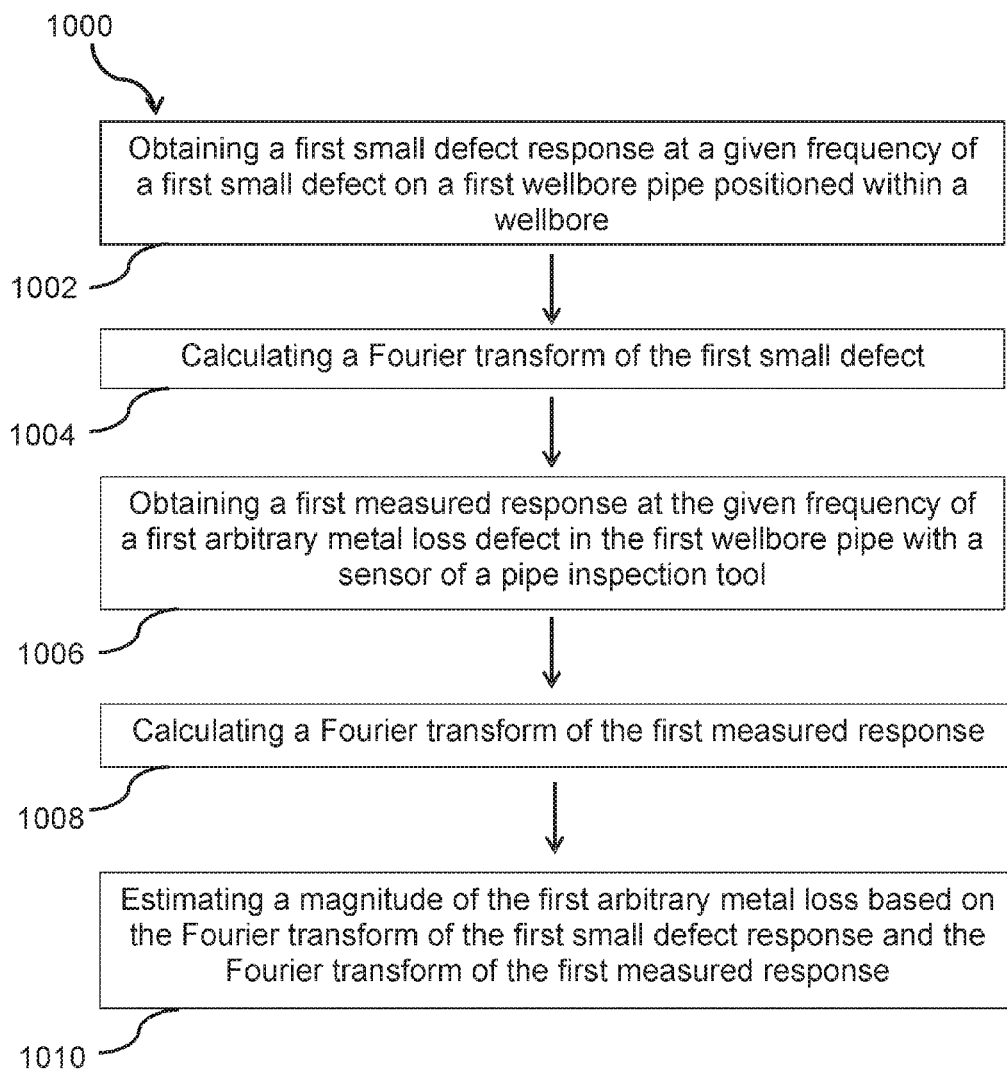
FIG. 10 is a schematic flowchart of an example method.

FIG. 10 is a schematic flowchart of an example method 1000, according to one or more embodiments of the disclosure. In the method, a first small defect response is obtained at a given frequency of a first small defect on a first wellbore pipe positioned within a wellbore, as at 1002. A Fourier transform of the first small defect response may then be calculated, as at 1004. A first measured response is then obtained at the given frequency of a first arbitrary metal loss defect in the first wellbore pipe with a sensor of a pipe inspection tool, as at 1006, and a Fourier transform of the first measured response is then calculated, as at 1008. The magnitude of the first arbitrary metal loss may then be estimated based on the Fourier transform of the first small defect response and the Fourier transform of the first measured response, as at 1010.

Figure 11:
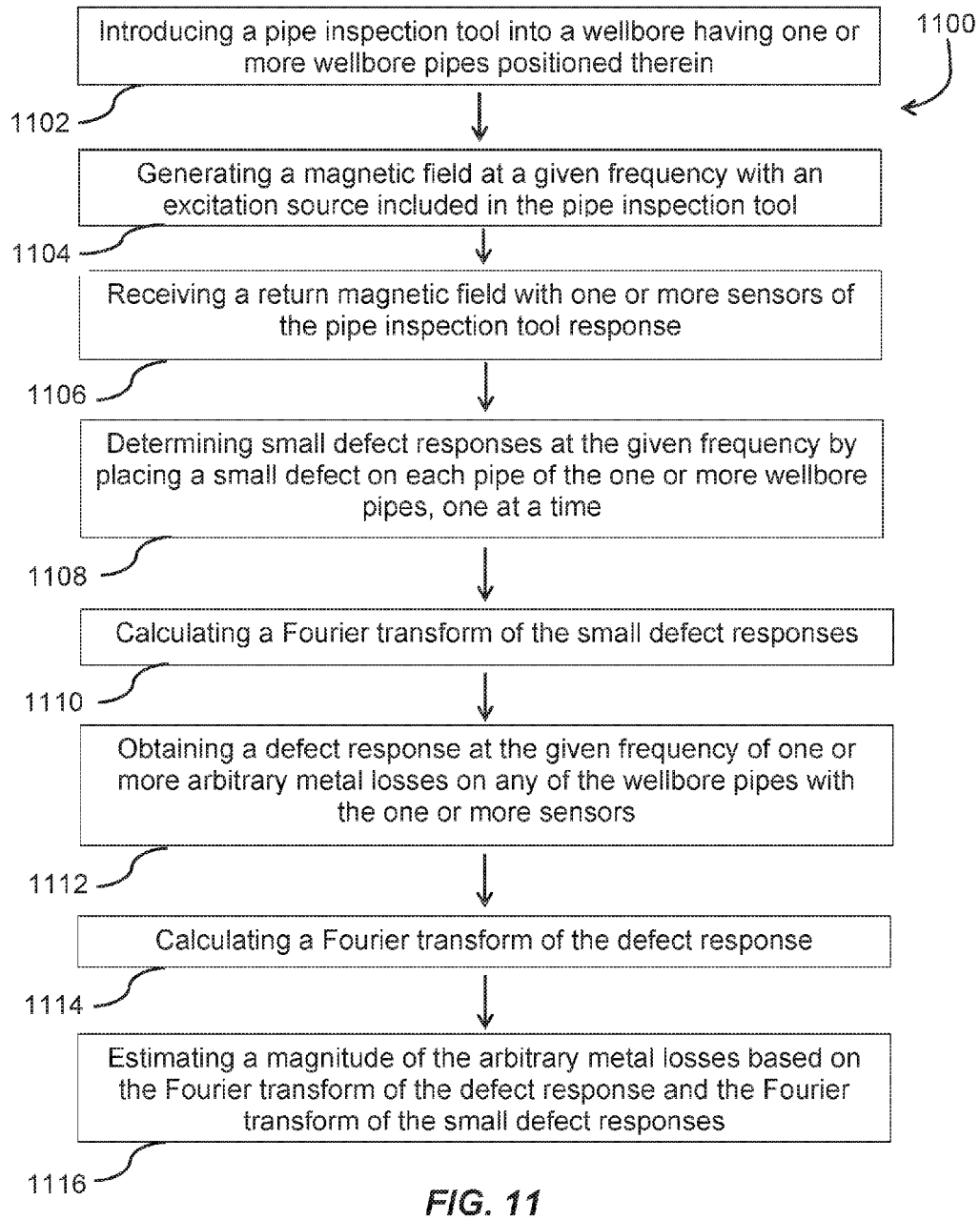
FIG. 11 is a schematic flowchart of another example method.

FIG. 11 is a schematic flowchart of another example method 1100, according to one or more embodiments of the disclosure. In the method 1100, a pipe inspection tool is introduced into a wellbore having one or more wellbore pipes positioned therein, as at 1102. A magnetic field is then generated at a given frequency with an excitation source included in the pipe inspection tool, as at 1104, and a return magnetic field is received with one or more sensors of the pipe inspection tool, as at 1106. Small defect responses are then determined at the given frequency by placing a small defect on each pipe of the one or more wellbore pipes, one at a time, as at 1108, and a Fourier transform of the small defect responses is calculated, as at 1110. A defect response is then obtained at the given frequency of one or more arbitrary metal losses on any of the wellbore pipes with the one or more sensors, as at 1112, and a Fourier transform of the defect response is then calculated, as at 1114. A magnitude of the arbitrary metal losses may then be estimated based on the Fourier transform of the defect response and the Fourier transform of the small defect responses, as at 1116.

Those skilled in the art will readily appreciate that the methods described herein may be undertaken using a computerized system, such as the computing facilities 122 of the logging facility 120 of FIG. 1. Computer hardware used to implement the various methods and algorithms described herein can include a processor configured to execute one or more sequences of instructions, programming stances, or code stored on a non-transitory, computer-readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. In some embodiments, computer hardware can further include elements such as, for example, a memory (e.g., random access memory (RAM), flash memory, read only memory (ROM), programmable read only memory (PROM), electrically erasable programmable read only memory (EEPROM)), registers, hard disks, removable disks, CD-ROMS, DVDs, or any other like suitable storage device or medium.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and/or software.

As used herein, a machine-readable medium will refer to any medium that directly or indirectly provides instructions to a processor for execution. A machine-readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Embodiments disclosed herein include:

A. A method that includes obtaining a first small defect response at a given frequency of a first small defect on a first wellbore pipe positioned within a wellbore, calculating a Fourier transform of the first small defect response, obtaining a first measured response at the given frequency of a first arbitrary metal loss defect in the first wellbore pipe with a sensor of a pipe inspection tool, calculating a Fourier transform of the first measured response; and estimating a magnitude of the first arbitrary metal loss based on the Fourier transform of the first small defect response and the Fourier transform of the first measured response.

B. A method that includes introducing a pipe inspection tool into a wellbore having one or more wellbore pipes positioned therein, generating a magnetic field at a given frequency with an excitation source included in the pipe inspection tool, receiving a return magnetic field with one or more sensors of the pipe inspection tool, determining small defect responses at the given frequency by placing a small defect on each pipe of the one or more wellbore pipes, one at a time, calculating a Fourier transform of the small defect responses, obtaining a defect response at the given frequency of one or more arbitrary metal losses on any of the wellbore pipes with the one or more sensors, calculating a Fourier transform of the defect response, and estimating a magnitude of the arbitrary metal losses based on the Fourier transform of the defect response and the Fourier transform of the small defect responses.

Each of embodiments A and B may have one or more of the following additional elements in any combination: Element 1: further comprising obtaining a second small defect response at the given frequency of a second small defect on a second wellbore pipe positioned within the wellbore, obtaining a second measured response at the given frequency of a second arbitrary metal loss defect in the second wellbore pipe with the sensor of the pipe inspection tool, calculating a second Fourier transform of the second measured response, and estimating a magnitude of the second arbitrary metal loss based on the Fourier transform of the first and second small defect responses and the Fourier transform of the first and second measured responses. Element 2: wherein obtaining the second small defect response comprises running a computer model with pipe parameter inputs. Element 3: wherein the pipe parameter inputs are calculated from a given well plan. Element 4: wherein the pipe parameter inputs are calculated from previous measurements. Element 5: wherein obtaining the second small defect response comprises running a surface experiment with a small defect. Element 6: further comprising calibrating the first small defect response to obtain a calibrated small defect response of the first small defect, calculating a Fourier transform of the calibrated small defect response, calibrating the first measured response to obtain a calibrated defect response of the first arbitrary metal loss defect, calculating a Fourier transform of the calibrated defect response, and estimating a magnitude of the first arbitrary metal loss based on the Fourier transform of the calibrated defect response and the Fourier transform of the calibrated small defect response. Element 7: further comprising obtaining a solution of an equation that involves the Fourier transform of the calibrated defect response and the Fourier transform of the calibrated small defect response, calculating the inverse Fourier transform of the solution, and imaging the first arbitrary metal loss in the first wellbore pipe based on the inverse Fourier transform of the solution. Element 8: wherein the given frequency comprises a plurality of frequencies, the method further comprising obtaining a solution of a system of equations that involves the Fourier transform of the calibrated defect response and the Fourier transform of the calibrated small defect response, calculating the inverse Fourier transform of the solution, and imaging the first arbitrary metal loss in the first wellbore pipe based on the inverse Fourier transform of the solution. Element 9: wherein calibrating the first small defect response comprises obtaining a first response at the given frequency with the sensor over a first portion of the first wellbore pipe without the first arbitrary metal loss defect, obtaining a second response at the given frequency with the sensor over a second portion of the first wellbore pipe with the first arbitrary metal loss defect, and subtracting the first and second responses to obtain the calibrated defect response. Element 10: wherein obtaining the first small defect response comprises modelling the first small defect based on wellbore pipe data stored in a library or a database. Element 11: wherein obtaining the first small defect response comprises obtaining the first measured response with the sensor of the pipe inspection tool. Element 12: wherein obtaining the first small defect response of the first small defect comprises approximating the first small defect with a Dirac delta function ?$(z, D_m/2)$ at a radial distance of $D_m/2$, where $z$ is an axial position of the first small defect within the wellbore and $D_m/2$ is a radial position away from a center of the wellbore.

Element 13: further comprising calibrating the small defect responses to obtain corresponding calibrated small defect responses of the small defects, calculating a Fourier transform of the calibrated small defect responses, calibrating the defect response to obtain a calibrated defect response of the arbitrary metal losses on any of the wellbore pipes, calculating a Fourier transform of the calibrated defect response, and estimating a magnitude of the arbitrary metal losses based on the Fourier transform of the calibrated defect response and the Fourier transform of the calibrated small defect responses. Element 14: further comprising obtaining a solution of an equation that involves the Fourier transform of the calibrated defect response and the Fourier transform of the calibrated small defect response, calculating the inverse Fourier transform of the solution, and imaging the arbitrary metal loss in the wellbore pipe based on the inverse Fourier transform of the solution. Element 15: wherein the given frequency comprises a plurality of frequencies, the method further comprising obtaining a solution of a system of equations that involves the Fourier transform of the calibrated defect response and the Fourier transform of the calibrated small defect responses acquired from all the pipes, calculating the inverse Fourier transform of the solution, and imaging the arbitrary metal loss at each wellbore pipe based on the inverse Fourier transform of the solution. Element 16: further comprising monitoring the one or more wellbore pipes within the wellbore at a plurality of selected depths within the wellbore, estimating magnitudes of the arbitrary metal losses in the one or more wellbore pipes at each of the plurality of selected depths, and combining the magnitudes to obtain a one-dimensional log of the wellbore at the selected depths.

By way of non-limiting example, exemplary combinations applicable to A and B include: Element 2 with Element 3; Element 2 with Element 4; Element 6 with Element 7; Element 6 with Element 8; Element 6 with Element 9; Element 13 with Element 14; and Element 13 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
   obtaining a first small defect response at a given frequency of a first small defect on a first wellbore pipe positioned within a wellbore;
   calculating a Fourier transform of the first small defect response;
   obtaining a first measured response at the given frequency of a first arbitrary metal loss defect in the first wellbore pipe with a sensor of a pipe inspection tool;
   calculating a Fourier transform of the first measured response; and
   estimating a magnitude of the first arbitrary metal loss based on the Fourier transform of the first small defect response and the Fourier transform of the first measured response.

2. The method of claim 1, further comprising:
   obtaining a second small defect response at the given frequency of a second small defect on a second wellbore pipe positioned within the wellbore;
   obtaining a second measured response at the given frequency of a second arbitrary metal loss defect in the second wellbore pipe with the sensor of the pipe inspection tool;
   calculating a second Fourier transform of the second measured response; and
   estimating a magnitude of the second arbitrary metal loss based on the Fourier transform of the first and second small defect responses and the Fourier transform of the first and second measured responses.

3. The method of claim 1, wherein obtaining the second small defect response comprises running a surface experiment with a small defect.

4. The method of claim 1, wherein obtaining the first small defect response comprises modelling the first small defect based on wellbore pipe data stored in a library or a database.

5. The method of claim 1, wherein obtaining the first small defect response comprises obtaining the first measured response with the sensor of the pipe inspection tool.

6. The method of claim 1, wherein obtaining the first small defect response of the first small defect comprises approximating the first small defect with a Dirac delta function $\delta(z, D_m/2)$ at a radial distance of $D_m/2$, where z is an axial position of the first small defect within the wellbore and $D_m/2$ is a radial position away from a center of the wellbore.

7. The method of claim 1, wherein obtaining the second small defect response comprises running a computer model with pipe parameter inputs.

8. The method of claim 7, wherein the pipe parameter inputs are calculated from a given well plan.

9. The method of claim 7, wherein the pipe parameter inputs are calculated from previous measurements.

10. The method of claim 1, further comprising:
    calibrating the first small defect response to obtain a calibrated small defect response of the first small defect;
    calculating a Fourier transform of the calibrated small defect response;
    calibrating the first measured response to obtain a calibrated defect response of the first arbitrary metal loss defect;
    calculating a Fourier transform of the calibrated defect response; and
    estimating a magnitude of the first arbitrary metal loss based on the Fourier transform of the calibrated defect response and the Fourier transform of the calibrated small defect response.

11. The method of claim 10, further comprising:
    obtaining a solution of an equation that involves the Fourier transform of the calibrated defect response and the Fourier transform of the calibrated small defect response;
    calculating the inverse Fourier transform of the solution; and
    imaging the first arbitrary metal loss in the first wellbore pipe based on the inverse Fourier transform of the solution.

12. The method of claim 10, wherein the given frequency comprises a plurality of frequencies, the method further comprising:
    obtaining a solution of a system of equations that involves the Fourier transform of the calibrated defect response and the Fourier transform of the calibrated small defect response;
    calculating the inverse Fourier transform of the solution; and
    imaging the first arbitrary metal loss in the first wellbore pipe based on the inverse Fourier transform of the solution.

13. The method of claim 10, wherein calibrating the first small defect response comprises:
    obtaining a first response at the given frequency with the sensor over a first portion of the first wellbore pipe without the first arbitrary metal loss defect;
    obtaining a second response at the given frequency with the sensor over a second portion of the first wellbore pipe with the first arbitrary metal loss defect; and
    subtracting the first and second responses to obtain the calibrated defect response.

14. A method, comprising:
    introducing a pipe inspection tool into a wellbore having one or more wellbore pipes positioned therein;
    generating a magnetic field at a given frequency with an excitation source included in the pipe inspection tool;
    receiving a return magnetic field with one or more sensors of the pipe inspection tool;
    determining small defect responses at the given frequency by placing a small defect on each pipe of the one or more wellbore pipes, one at a time;
    calculating a Fourier transform of the small defect responses;

obtaining a defect response at the given frequency of one or more arbitrary metal losses on any of the wellbore pipes with the one or more sensors;

calculating a Fourier transform of the defect response; and estimating a magnitude of the arbitrary metal losses based on the Fourier transform of the defect response and the Fourier transform of the small defect responses.

15. The method of claim 14, further comprising:

monitoring the one or more wellbore pipes within the wellbore at a plurality of selected depths within the wellbore;

estimating magnitudes of the arbitrary metal losses in the one or more wellbore pipes at each of the plurality of selected depths; and combining the magnitudes to obtain a one-dimensional log of the wellbore at the selected depths.

16. The method of claim 14, further comprising:

calibrating the small defect responses to obtain corresponding calibrated small defect responses of the small defects;

calculating a Fourier transform of the calibrated small defect responses;

calibrating the defect response to obtain a calibrated defect response of the arbitrary metal losses on any of the wellbore pipes;

calculating a Fourier transform of the calibrated defect response; and estimating a magnitude of the arbitrary metal losses based on the Fourier transform of the calibrated defect response and the Fourier transform of the calibrated small defect responses.

17. The method of claim 16, further comprising:

obtaining a solution of an equation that involves the Fourier transform of the calibrated defect response and the Fourier transform of the calibrated small defect response;

calculating the inverse Fourier transform of the solution; and imaging the arbitrary metal loss in the wellbore pipe based on the inverse Fourier transform of the solution.

18. The method of claim 16, wherein the given frequency comprises a plurality of frequencies, the method further comprising:

obtaining a solution of a system of equations that involves the Fourier transform of the calibrated defect response and the Fourier transform of the calibrated small defect responses acquired from all the pipes;

calculating the inverse Fourier transform of the solution; and imaging the arbitrary metal loss at each wellbore pipe based on the inverse Fourier transform of the solution.

* * * * *